United States Patent [19]

Aasen

[11] Patent Number: 4,553,941

[45] Date of Patent: Nov. 19, 1985

[54] ACETAL AND HEMIACETAL DENTIN AND ENAMEL ADHESIVE PRIMERS

[75] Inventor: Steven M. Aasen, Lakeland, Minn.

[73] Assignee: Minnesota Mining and Manufacturing Company, St. Paul, Minn.

[21] Appl. No.: 662,729

[22] Filed: Oct. 19, 1984

[51] Int. Cl.$^4$ ................................................ A61K 6/08
[52] U.S. Cl. .................................... 433/228.1; 106/35
[58] Field of Search ........................... 106/35; 433/217

[56] References Cited

U.S. PATENT DOCUMENTS

| | | | |
|---|---|---|---|
| 4,182,035 | 8/1977 | Yamauchi | 433/228 |
| 4,222,780 | 4/1978 | Shibatani | 106/35 |
| 4,235,633 | 1/1979 | Tomioka | 106/35 |

FOREIGN PATENT DOCUMENTS 058483  1/1982  European Pat. Off. .

OTHER PUBLICATIONS

Munksgaard & Asmussen, J. Dent. Res., 63, 8, pp. 1087–1089 (Aug., 1984).

*Primary Examiner*—Lorenzo B. Hayes
*Attorney, Agent, or Firm*—Donald M. Sell; James A. Smith; David R. Cleveland

[57] ABSTRACT

Acetals and hemiacetals are used as primers for dentin and enamel adhesives.

8 Claims, No Drawings

ACETAL AND HEMIACETAL DENTIN AND ENAMEL ADHESIVE PRIMERS

TECHNICAL FIELD

This invention relates to primer compositions for use with dentin and enamel adhesives, and with dental composites, restoratives, and orthodontic bracket adhesives. This invention also relates to a method for repairing, adhering to, or altering the position of teeth through the use of such compositions.

BACKGROUND ART

In recent years there has been intense interest in the dental field in adhesives which bond to dentin. Recent examples of such adhesives include those described in U.S. Pat. Nos. 4,182,035, 4,222,780, 4,235,633, and U.S. Ser. No. 234,560, filed Feb. 13, 1981). Primer compositions for use on dentin in conjunction with existing enamel adhesives are disclosed in Danish Patent Application No. 4898-83 and in Munksgaard and Asmussen, *J. Dent. Res.*, 63, 8, pp 1087–1089 (August, 1984). In general, the mechanism by which such adhesive and primer compositions function is poorly understood and the subject of current speculation.

SUMMARY OF INVENTION

The present invention provides, in one aspect, a primer-coated dentin surface comprising a layer of a liquid primer composition comprising acetal or hemiacetal adjacent said dentin surface. The present invention also provides a method for use of such a composition for repairing, adhering to, or altering the position of teeth. The invention enhances the adhesion of existing enamel adhesives to dentin.

DETAILED DESCRIPTION

The acetals and hemiacetals used in the present invention are liquids, or are solids that can be dissolved in a solvent which does not interfere with the stability or functioning of the primer composition. The acetals and hemiacetals used in the present invention are suitable for use in the oral environment (e.g., not appreciably irritating to the pulp) and enhance the adhesion of enamel adhesives to dentin. The acetals and hemiacetals are in some instances commercially available, and can be prepared using methods familiar to those skilled in the art of organic synthesis.

Preferred acetals for use in the present invention have the formula

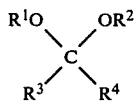
                    I where $R^1$ and $R^2$ are organic groups, $R^3$ and $R^4$ are hydrogen or organic groups, $R^1$ through $R^4$ can be the same or different, and where any two or more $R^1$ through $R^4$ can join together with the carbon atom C in formula I to form a cyclic ring.

Preferred hemiacetals for use in the present invention have the formula

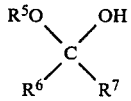
                    II where $R^5$ is an organic group, $R^6$ and $R^7$ are hydrogen or organic groups, $R^5$ through $R^7$ can be the same or different, and where any two or more of $R^5$ through $R^7$ can join together with the carbon atom C in formula II to form a cyclic ring.

In formulas I and II above, $R^1$ through $R^7$ can contain substituents, heteroatoms, or unsaturated linkages which do not interfere with the stability or functioning of the primer composition. Suitable substituents on $R^1$ through $R^7$ include halo, cyano, vinyl, aryl and alkyl, with methacryloyl and acryloyl substituents being preferred. Also preferred are acetals and hemiacetals containing one or more cyclic groups capable of ring opening when used on teeth. Suitable heteroatoms include N, O, P and S atoms.

Acetals for use in the present invention include the following compounds:

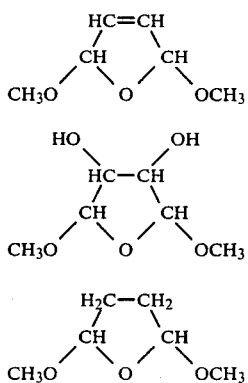

Hemiacetals for use in the present invention include:

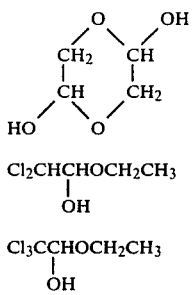

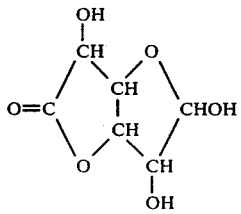

Mixtures of acetals and/or hemiacetals can be used if desired.

Suitable solvents include water, lower alkyl alcohols such as ethanol and isopropanol and acetone. Water is a preferred solvent. The primer composition should contain sufficient acetal or hemiacetal to enable the formation of a bond to dentin.

The primer compositions of the present invention preferably are applied to a dentin surface that has been freshly cut (e.g., with a bur) and rinsed with clean water, leaving the so-called "smear layer" relatively intact. A layer of dentin or enamel adhesive, or a layer of a dental composite, restorative, or orthodontic bracket adhesive composition, or layers of each, are applied over the primer and cured. For some acetals and hemiacetals it is advantageous to wash the abraded, rinsed dentin surface with a pretreatment solution prior to application of the primer composition. Suitable pretreatment solutions include ethylenediamine tetracetic acid ("EDTA") and citric acid. Optimum performance is obtained if the pretreatment solution is buffered or otherwise adjusted to a pH which maximizes adhesion to dentin. Adjustment of pH in the pretreating solution can be carried out emperically, with selection of the desired pH level being based upon the degree of dentin adhesion desired. A pretreatment solution is not required in all instances.

If necessary, the primer composition can contain a diluent (e.g., water, ethanol, or acetone) to insure that the composition properly wets the dentin surface.

For some acetals and hemiacetals, adhesion is improved if an active hydrogen-functional comonomer is mixed with the dentin primer composition. Suitable comonomers include hydroxyalkyl acrylates and methacrylates such as hydroxyethyl methacrylate ("HEMA"), and nitrogen containing monomers such as N-methylolacrylamide, hydroxyalkylmethyacrylamide, and N-vinyl pyrollidone. Selection of the type and amount of comonomer can be carried out emperically to obtain the desired level of dentin adhesion. A comonomer is not required in all instances.

The dentin primer compositions of the invention preferably are overcoated with conventional dentin or enamel adhesives and, if desired, further overcoated with a dental composite, restorative, or orthodontic bracket adhesive composition. The layer or layers are cured and finished using conventional techniques.

Adhesion to dentin of the primer compositions of the invention was evaluated as follows. Extracted bovine teeth were mounted in methacrylate resin discs and ground flat using several grades of "WETORDRY" abrasive paper (ending with 600 grit), to expose a flat dentin surface. Each ground dentin surface was water rinsed and dried using filtered air. A pretreatment solution (made from a saturated aqueous solution of EDTA whose pH was adjusted to a variety of values using sodium hydroxide) was applied to the dentin surface and allowed to stand for one minute followed by a ten second water rinse and a jet of filtered air to dry the dentin surface. The primer composition (made from a 3.5 weight percent aqueous solution of the acetal or hemiacetal, containing in some instances 35 weight percent HEMA) was applied to the dentin surface with a cotton swab. After one minute, the dentin surface was given a ten second water rinse and dried with a jet of filtered air. The dentin surface was overcoated with a thin layer of enamel adhesive ("Concise Enamel Bond" resin, commercially available from 3M) or in some instances with a thin layer of dentin adhesive ("Scotchband Dental Adhesive", commercially available from 3M), then overcoated with a 2.5 mm thick by 2.5 mm diameter cylindrical molded plug of restorative ("Silux" Light Cured Restorative, commercially available from 3M). The resulting assembly was irradiated for 20 seconds using a dental curing light ("Visulux" dental curing light, commercially available from 3M). The cured assembly was placed in 37° C. water for 24 hours, and then the mold was removed. The bond strength was tested by placing a loop of orthodontic wire around the plug at its base, clamping the methacrylate resin disc and the wire in opposing jaws of an "Instron" tensile testing apparatus and stressing the primer bond in the shear direction (i.e., in a direction parallel to the ground dentin surface) at a crosshead separation rate of 0.05 centimeters/minute. The shear strength was calculated by measuring the load at breakage and dividing by the cross-sectional area of the bonded dentin surface. Five replications were performed for each sample. The reported adhesion values are the average of all five samples, including any values of zero obtained during testing.

The following examples are offered to aid understanding of the present invention and are not to be construed as limiting the scope thereof.

EXAMPLES 1-8

Using the procedure outlined above, the shear strength on dentin of several acetals and hemiacetals was evaluated. Set out below in Table I are the example number, pH of the pretreatment solution, type of acetal or hemiacetal, type of coreactant (if any) in the primer composition, and the shear strength obtained.

TABLE I

| Example Number | pH of pretreatment solution | Acetal or hemiacetal | Coreactant | Shear strength, $Kg/cm^2$ |
|---|---|---|---|---|
| 1 | 7.4 | 2,5-dimethoxy-2,5-dihydrofuran | — | 25.2 |
| 2 | 7.4 | 2,5-dimethoxy-2,5-dihydrofuran | HEMA | 24.4 |
| 3 | 3 | 2,5-dimethoxy-2,5-dihydrofuran | — | 0.0 |
| 4 | 3 | 2,5-dimethoxy-2,5-dihydrofuran | HEMA | 17.7 |
| 5 | 7.4 | glucaronic acid 3,6-lactone | — | 13.0 |
| 6 | 7.4 | glucaronic acid 3,6-lactone | HEMA | 21.6* |
| 7 | 7.4 | glucaronic acid 3,6-lactone | — | 33.7** |
| 8 | 7.4 | glucaronic acid 3,6-lactone | HEMA | 46.4** |

*Average of 10 instead of 5 samples
**bonded with "Scotchbond Dental Adhesive" instead of "Concise Enamel Bond" resin The typical bond strength on dentin of an enamel adhesive such as "Concise Enamel Bond" is zero. Thus, these examples illustrate that the primer compositions of the invention significantly enhance the bond strength on dentin of such enamel adhesives. These examples also illustrate the formation of bonds to dentin using a variety of acetals and hemiacetals with and without a variety of coreactants.

Various modifications and alterations of this invention will be apparent to those skilled in the art without departing from the scope and spirit of this invention and the latter should not be restricted to that set forth herein for illustrative purposes.

I claim:

1. A primer-coated dentin surface comprising a layer of a liquid primer composition comprising acetal or hemiacetal adjacent said dentin surface.

2. A primer-coated dentin surface according to claim 1, wherein said primer comprises acetal.

3. A primer-coated dentin surface according to claim 2, wherein said acetal comprises 2,5-dimethoxy-2,5-dihydrofuran.

4. A primer-coated dentin surface according to claim 1, wherein said primer comprises hemiacetal.

5. A primer-coated dentin surface according to claim 4, wherein said hemiacetal comprises glucaronic acid 3,6-lactone.

6. A primer-coated dentin surface according to claim 1, wherein said acetal or hemiacetal has at least one methacryloyl or acryloyl substituent.

7. A primer-coated dentin surface according to claim 1, wherein said acetal or hemiacetal contains one or more cyclic groups capable of ring opening when used on teeth.

8. A method for repairing, adhering to, or altering the position of a tooth, comprising the steps of
(a) applying to dentin on said tooth a layer of a liquid primer composition comprising acetal or hemiacetal,
(b) overcoating said layer with a dentin or enamel adhesive, and
(c) curing said adhesive.

* * * * *